United States Patent
Masere et al.

(10) Patent No.: US 9,957,209 B2
(45) Date of Patent: May 1, 2018

(54) USE OF QUINONE METHIDES AS ANTIPOLYMERANTS FOR VINYLIC MONOMERS

(71) Applicant: Ecolab USA Inc., St. Paul, MN (US)

(72) Inventors: Jonathan Masere, Richmond, TX (US); Ramon Colorado, Jr., Houston, TX (US)

(73) Assignee: Ecolab USA Inc., St. Paul, MN (US)

( * ) Notice: Subject to any disclaimer, the term of this patent is extended or adjusted under 35 U.S.C. 154(b) by 17 days.

(21) Appl. No.: 15/085,523

(22) Filed: Mar. 30, 2016

(65) Prior Publication Data

US 2016/0289147 A1    Oct. 6, 2016

Related U.S. Application Data

(60) Provisional application No. 62/140,907, filed on Mar. 31, 2015.

(51) Int. Cl.
*C07C 7/20* (2006.01)
*C09K 15/08* (2006.01)

(52) U.S. Cl.
CPC ............... *C07C 7/20* (2013.01); *C09K 15/08* (2013.01)

(58) Field of Classification Search
CPC ..................... C07C 7/20; C09K 15/08
See application file for complete search history.

(56) References Cited

U.S. PATENT DOCUMENTS

| | | |
|---|---|---|
| 2,455,745 A | 12/1948 | Erickson |
| 2,783,271 A | 2/1957 | Eck et al. |
| 2,810,651 A | 10/1957 | Thompson |
| 2,965,685 A | 12/1960 | Campbell |
| 3,222,334 A | 12/1965 | Demme |
| 3,320,305 A | 5/1967 | Wiese |
| 3,696,050 A | 10/1972 | Werts, III et al. |
| 3,704,235 A | 11/1972 | Rassat et al. |
| 4,202,742 A | 5/1980 | Castle |
| 4,293,347 A | 10/1981 | Haschke et al. |
| 4,487,981 A | 12/1984 | Miller et al. |
| 5,221,498 A | 6/1993 | Reid et al. |
| 5,235,056 A | 8/1993 | Cunkle et al. |
| 5,290,888 A | 3/1994 | Gatechair et al. |
| 5,426,257 A | 6/1995 | Arhancet |
| 5,489,720 A | 2/1996 | Arhancet |
| 5,648,574 A | 7/1997 | Arhancet et al. |
| 5,670,692 A | 9/1997 | Nesvadba et al. |
| 5,728,305 A | 3/1998 | Hawkinson |
| 5,728,872 A | 3/1998 | Riemenschneider |
| 5,750,765 A | 5/1998 | Nesvadba et al. |
| 5,773,674 A | 6/1998 | Arhancet et al. |
| 5,932,735 A | 8/1999 | Cunkle et al. |
| 6,180,231 B1 | 1/2001 | Keogh |
| 6,284,936 B2 | 9/2001 | Shahid |
| 6,342,647 B1 | 1/2002 | Roof et al. |
| 6,500,982 B1 | 12/2002 | Hale et al. |
| 6,525,146 B1 | 2/2003 | Shahid |
| 6,599,326 B1 | 7/2003 | Seltzer et al. |
| 6,686,422 B2 | 2/2004 | Shahid |
| 6,770,222 B1 | 8/2004 | Ukita et al. |
| 7,066,990 B2 | 6/2006 | Wood et al. |
| 7,132,540 B1 | 11/2006 | Jawdosiuk et al. |
| 7,282,136 B2 | 10/2007 | Howdeshell |
| 7,309,682 B2 | 12/2007 | Lupia et al. |
| 7,429,545 B2 | 9/2008 | Lupia et al. |
| 7,618,644 B2 | 11/2009 | Lupia et al. |
| 7,718,096 B2 | 5/2010 | Yale et al. |
| 7,943,809 B2 | 5/2011 | Benage et al. |
| 8,110,650 B2 | 2/2012 | Nava et al. |
| 8,247,593 B2 | 8/2012 | Morrison et al. |
| 8,691,944 B2 | 4/2014 | Clark et al. |
| 8,884,038 B2 | 11/2014 | Masere |
| 2009/0287013 A1 | 11/2009 | Morrison et al. |
| 2010/0168434 A1 | 7/2010 | Loyns et al. |
| 2012/0056128 A1 | 3/2012 | Thoret Bauchet |
| 2012/0313036 A1 | 12/2012 | Masere |
| 2013/0178652 A1 | 7/2013 | Fruchey et al. |
| 2014/0288337 A1* | 9/2014 | Rinker ...................... C07C 7/20 585/4 |

FOREIGN PATENT DOCUMENTS

| | | |
|---|---|---|
| CA | 2232502 | 9/1998 |
| CA | 2 260 310 A1 | 7/2000 |
| CN | 102795966 A | 11/2012 |
| DE | 102008061611 A1 | 6/2009 |

(Continued)

OTHER PUBLICATIONS

Jurd, L., et al., "New Types of Insect Chemosterilants. Benzylphenols and Benzyl-1,3-benzodioxole Derivatives as Additives to Housefly Diet," Journal of Agricultural and Food Chemistry, 1979, pp. 1007-1016, vol. 27, No. 5.
Synthesis of Tropine & Its Derivatives, accessed from http://www.lab-q.net/synthesis/syn-tropine on Dec. 18, 2014, 6 pages.
King, Frank D., Bioisosteres, Conformational Restriction, and Prodrugs—Case History: An Example of a Conformational Restriction Approach, Med. Chem., Principle and Practice (1994), pp. 206-208.
Ma, Yun, Nitroxides in Mechanistic Studies; Ageing of Gold Nanoparticles and Nitroxide Transformation in Acids, Submitted to the Department of Chemistry, University of York, 2010, 221 pages.
Miyazawa, Takeo et al., New Method for Preparation of Superoxide Ion by Use of Amino Oxide, J. Org. Chem., Dec. 1985, vol. 50, No. 25, pp. 5389-5391.
Sciannamea, Valerie et al., In-Situ Nitroxide-Mediated Radical Polymerization (NMP) Processes: Their Understanding and Optimization, Chem. Rev. 2008, vol. 108, No. 3, pp. 1104-1126.

*Primary Examiner* — In Suk C Bullock
*Assistant Examiner* — Alyssa L Cepluch
(74) *Attorney, Agent, or Firm* — Senniger Powers LLP

(57) ABSTRACT

The present invention generally relates to compounds and methods for inhibiting the radical polymerization of unsaturated compounds, particularly vinyl monomers. More particularly, it relates to the use of cinnamyl quinone methides to inhibit the polymerization of unsaturated hydrocarbon compounds (e.g., vinyl monomers) soluble in organic solvents, particularly hydrocarbon streams.

20 Claims, No Drawings

(56) References Cited

FOREIGN PATENT DOCUMENTS

| | | |
|---|---|---|
| EP | 0 373 636 A1 | 6/1990 |
| EP | 0 765 856 A1 | 4/1997 |
| EP | 0 915 108 A1 | 5/1999 |
| EP | 0 943 665 A1 | 9/1999 |
| WO | 01/12677 A1 | 2/2001 |
| WO | 01/40404 A1 | 6/2001 |
| WO | 2006/078123 A1 | 7/2006 |
| WO | 2007/045886 A1 | 4/2007 |
| WO | 2008/103613 A2 | 8/2008 |
| WO | 2015/084843 A1 | 6/2015 |

* cited by examiner

USE OF QUINONE METHIDES AS ANTIPOLYMERANTS FOR VINYLIC MONOMERS

CROSS-REFERENCE TO RELATED APPLICATION

This application claims priority to U.S. Provisional Patent Application Ser. No. 62/140,907 filed on Mar. 31, 2015, the disclosure of which is incorporated herein by reference in its entirety.

FIELD OF THE INVENTION

The present invention generally relates to compounds and methods for preventing the free-radical polymerization of unsaturated compounds, particularly vinyl aromatic and difunctional monomers. More particularly, the invention relates to the use of cinnamyl quinone methides to inhibit the polymerization of unsaturated compounds notably, vinyl monomers characteristic of petrochemical hydrocarbon streams.

BACKGROUND OF THE INVENTION

Unsaturated compounds, particularly vinyl monomers found in hydrocarbon streams, can undesirably polymerize at various stages of their manufacture, processing, handling, storage, and use. Vinyl monomers can undergo self-initiated polymerization at elevated temperatures even in the absence of polymerization promoters. This undesired thermal polymerization can be a problem during the purification of vinyl aromatic monomers and during sudden process shutdowns. Undesirable polymerization results in product loss because the valuable monomer, the end product, is consumed in the undesired side reaction. Moreover, polymerization reduces production efficiency as the polymer is deposited on process equipment. This fouling of process equipment may require unscheduled shutdown to remove the undesired polymer by physical methods.

Currently, there are antipolymerants that are in use, most notably dinitro-substituted aromatic compounds. Despite their antipolymerant efficacy and low cost, dinitrophenols (DNP), which include 2,6-dinitrophenol, 2,4-dinitrocresol, and 2-sec-butyl-4,6-dinitrophenol (DNBP)) compounds, are highly toxic, particularly DNBP. In the case of the purification of styrene, the dominant product in the market is DNBP. In spite of its high antipolymerant performance, DNBP is highly toxic and has a deleterious environmental impact. Consequently, the use of DNBP is becoming highly restricted, for example its usage under the restrictive European REACH legislation. There is a need for alternative antipolymerants that are as efficient as DNBP at reducing polymerization and yet are safe and environmentally friendly.

SUMMARY OF THE INVENTION

One aspect of the present invention is a method for inhibiting polymerization of unsaturated compounds whereby said compounds are in contact with an effective amount of a quinone methide compound of Formula 1:

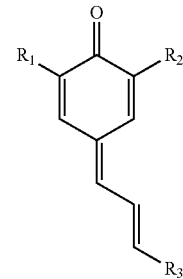

(1)

wherein $R_1$ and $R_2$ are independently hydrogen, $C_4$ to $C_{18}$ alkyl, $C_5$ to $C_{12}$ cycloalkyl, aryl, $C_7$ to $C_{15}$ alkylaryl, or $C_7$ to $C_{15}$ arylalkyl; and $R_3$ is hydrogen, $C_1$-$C_{18}$ alkyl, $C_5$-$C_{12}$ cycloalkyl, aryl, or $C_7$-$C_{15}$ arylalkyl.

Another aspect of the invention is a composition for inhibiting undesirable polymerization of a vinyl monomer in a liquid hydrocarbon stream, the composition comprising: an effective amount of a quinone methide compound of Formula 1.

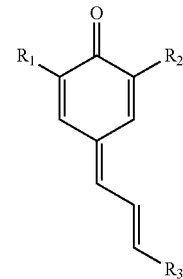

(1)

wherein $R_1$ and $R_2$ are independently hydrogen, $C_4$ to $C_{18}$ alkyl, $C_5$ to $C_{12}$ cycloalkyl, aryl, $C_7$ to $C_{15}$ alkylaryl, or $C_7$ to $C_{15}$ arylalkyl; $R_3$ is hydrogen, $C_1$-$C_{18}$ alkyl, $C_5$-$C_{12}$ cycloalkyl, aryl, $C_7$ to $C_{15}$ alkylaryl, or $C_7$-$C_{15}$ arylalkyl; and a suitable hydrocarbon solvent.

DESCRIPTION OF THE PREFERRED EMBODIMENTS

The present invention is a method for the prevention of unwanted polymerization of unsaturated compounds whereby said compounds are in contact with an effective amount of a quinone methide compound of Formula 1. Typical hydrocarbon streams comprise unsaturated compounds that are reactive and liable to unwanted polymerization under processing, transportation and storage conditions. The undesired polymerization of the unsaturated compounds is costly due to the loss of the desired monomer product. Moreover, the polymer deposits on the processing equipment such that the foulants polymer has to be removed by physical means. To remove the foulant, the process has to be shutdown, which is quite costly. Thus, methods for the prevention of the formation of this unwanted polymerization are beneficial.

To this end, particularly, the use of 7-cinnamyl substituted quinone (7-Cinn-QM) methide derivatives for the prevention of the polymerization of vinylic monomers during purification, transportation, and storage is disclosed. These quinone methide derivatives are non-toxic compounds.

In addition to this non-toxicity, 7-Cinn-QM derivatives do not contain sulfur or nitrogen, a feature that eliminates potential $NO_x$ and $SO_x$ gas emissions upon the incineration of waste streams containing said quinone methides. Equally significant is the elimination of the source of $NO_x$ gases that form heat-sensitive and explosive gums with divinylic species like butadiene. The use of 7-Cinn-QM derivatives as antipolymerants in the primary ethylene applications eliminates nitrogenous antipolymerants that may yield said explosive $NO_x$-based gums.

One aspect of the invention is a method for inhibiting polymerization of an unsaturated compound whereby said compound is in contact with an effective amount of a substituted quinone methide compound of Formula 1:

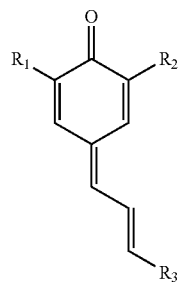

(1)

wherein $R_1$ and $R_2$ can independently be hydrogen, $C_4$ to $C_{18}$ alkyl, $C_5$ to $C_{12}$ cycloalkyl, aryl, $C_7$ to $C_{15}$ alkylaryl or $C_7$ to $C_{15}$ arylalkyl; and $R_3$ can be hydrogen, $C_1$-$C_{18}$ alkyl, $C_5$-$C_{12}$ cycloalkyl, aryl, $C_7$ to $C_{15}$ alkylaryl or $C_7$ to $C_{15}$ arylalkyl.

For the substituted quinone methide compound of Formula 1, the aryl group of $R_1$, $R_2$, or $R_3$ can be -phenylene-$R_4$, where $R_4$ can be hydrogen, $C_1$-$C_{18}$ alkyl, $C_5$-$C_{12}$ cycloalkyl, $C_5$-$C_{12}$ heterocycloalkyl, aryl, $C_7$-$C_{15}$ phenylalkyl, —COOH and —COOR$_5$, where $R_5$ can independently be selected from $C_1$-$C_{18}$ alkyl, $C_5$-$C_{12}$ cycloalkyl, aryl and $C_7$-$C_{15}$ arylalkyl. Preferably, the aryl group comprises —$C_6H_4$—$R_4$; wherein $R_4$ can be hydrogen, $C_1$-$C_3$ alkyl, —COOH and —COOR$_5$, wherein $R_5$ can be $C_1$-$C_3$ alkyl, or aryl.

Additionally, the substituted quinone methide compound of Formula 1 can have $R_1$ and $R_2$ independently selected from $C_4$-$C_{18}$ alkyl, $C_5$-$C_{12}$ cycloalkyl, aryl, and $C_7$-$C_{15}$ alkylaryl. Preferably, for Formula 1, $R_1$ and $R_2$ can be independently selected from $C_4$-$C_{18}$ alkyl.

The compounds of Formula 1 can have $R_1$ and $R_2$ independently selected from t-butyl, t-amyl, t-hexyl, t-octyl, and t-decyl. Preferably, for compounds of Formula 1, $R_1$ and $R_2$ can be independently selected from t-butyl, t-amyl, and t-octyl.

Further, the compounds of Formula 1 can have $R_3$ be hydrogen, $C_1$-$C_{18}$ alkyl, $C_5$-$C_{12}$ cycloalkyl, $C_5$-$C_{12}$ heterocycloalkyl, aryl, or $C_7$-$C_{15}$ arylalkyl.

For the methods described herein, the compounds of Formula 1 can have $R_3$ be hydrogen.

Further, the compounds of Formula 1 can have $R_3$ be $C_1$-$C_{18}$ alkyl.

Additionally, the compounds of Formula 1 can have $R_3$ be $C_5$-$C_{12}$ cycloalkyl.

Also, the compounds of Formula 1 can have $R_3$ be $C_5$-$C_{12}$ heterocycloalkyl.

The compounds of Formula 1 can have $R_3$ be $C_7$-$C_{15}$ arylalkyl.

Further, the compounds of Formula 1 can have $R_3$ be aryl.

The compounds of Formula 1 can also have $R_3$ be phenyl.

For the methods described herein, the compounds of Formula 1 can have $R_1$ and $R_2$ independently be t-butyl, t-amyl, t-hexyl, t-octyl, or t-decyl, and $R_3$ can be aryl.

For the methods described herein, the compounds of Formula 1 can have $R_1$ and $R_2$ independently be t-butyl, t-amyl, or t-octyl, and $R_3$ can be aryl.

For the methods described herein, the compounds of Formula 1 can have $R_1$ and $R_2$ independently be t-butyl, t-amyl, t-hexyl, t-octyl, or t-decyl, and $R_3$ can be phenyl.

For the methods described herein, the compounds of Formula 1 can have $R_1$ and $R_2$ be t-butyl, and $R_3$ can be aryl.

For the methods described herein, the compounds of Formula 1 wherein $R_1$ and $R_2$ can be t-butyl substituents, and $R_3$ can be a phenyl moiety.

For the methods described herein, the unsaturated compound can be ethylene, propylene, acetylene, styrene, vinyl chloride, vinyl alcohol esters such as vinyl acetate, acrylonitrile, an acrylate ester, a methacrylate ester, acrylic acid, methacrolein, acrolein, butadiene, indene, divinylbenzene, isoprene, acetylene, butylenes, vinyl acetylene, cyclopentadiene, and other unsaturated hydrocarbons known in the art as well as a combination thereof.

Preferably, the unsaturated compound can be ethylene, styrene, an acrylate ester, a methacrylate ester, or a combination thereof.

The unsaturated compound can be a constituent of a hydrocarbon stream under process, transportation, and storage.

Further, the vinyl monomer can be a constituent of a hydrocarbon stream undergoing a process of primary fractionation, a process-gas compression, acid-gas removal, light ends fractionation, quench water towers for gas crackers, dilution steam systems, styrene purification, acrylate purification, methacrylate purification, acrylic acid purification, methacrylic acid purification, acrolein purification, butadiene extraction, transportation, storage, propane dehydrogenation, diesel and petrol fuel stabilization, non-aromatic halogenated vinyl fractionation, non-aromatic halogenated vinyl stabilization, olefin metathesis process, hydroxyhydrocarbon purification, or a combination thereof.

Another aspect of the invention is a composition comprising a compound of Formula 1 and a solvent. As examples, suitable solvents include organic solvents such as pentane, heptane, hexane, benzene, ethylbenzene, toluene, ethylene glycol, butyl carbitol, alcohols, or a combination thereof. Other suitable solvents can also be used.

The composition can comprise one or more additional polymerization inhibitors. Compounds that are suitable as additional polymerization inhibitors in the inventive composition include phenols, alkylated phenols, nitrophenols, nitrosophenols, quinones, hydroquinones, alkylated hydroquinones, phenylenediamines, phenylenediimines, diphenylamines, quinone ethers, quinone methides, amines, hydroxylamines, and phenothiazines.

For the methods and compositions described herein, the polymerization reactions that are inhibited are preferably, undesired or unwanted polymerization reactions.

In a preferred aspect of the invention, the vinyl monomer is soluble in an organic solvent, particularly a hydrocarbon solvent.

The inventive method is used to prevent the polymerization of vinyl monomers during manufacture, purification, or storage processes. The method is particularly useful to inhibit polymerization during the distillation of vinyl monomers, such as styrene acrylates and olefins.

The antipolymerant compositions described herein can be introduced into the monomer to be protected by any conventional method. It can be added as a concentrated solution in suitable solvents just upstream of the point of desired application by suitable means. In addition, these compounds can be injected separately into the distillation train with the incoming feed, or through separate entry points providing efficient distribution of the inhibitor composition. Since the inhibitor is gradually depleted during operation, it is generally necessary to maintain the appropriate amount of the inhibitor in the distillation apparatus by adding inhibitor during the course of the distillation process. This addition may be carried out either on a generally continuous basis or by intermittently charging inhibitor into the distillation system if the concentration of inhibitor is to be maintained above the minimum required level.

The polymerization inhibiting compounds of this invention are also suited for protecting the reboiler sections of a distillation column.

The effective amount of substituted quinone methide compound of formula 1 can be an amount sufficient to inhibit polymerization of the unsaturated compounds. The conditions, such as presence of contaminants in the system and the process temperature, of the system under which the unsaturated compound is being processed will determine the amount of the quinone methide compound of formula 1 used. Accordingly, larger amounts of the quinone methide compound of formula 1 are required at higher processing temperatures and monomer with higher concentrations of contaminants.

The effective amount of the quinone methide compound of formula 1 ranges from about 1 ppm to about 10,000 ppm, from about 1 ppm to about 8000 ppm, from about 1 ppm to about 6000 ppm, from about 1 ppm to about 5000 ppm, from about 1 ppm to about 4000 ppm, from about 1 ppm to about 2000 ppm, or from about 1 ppm to about 1000 ppm based on the weight of the unsaturated compound. Preferably, the effective amount will range from about 1 ppm to about 1000 ppm based on the weight of the unsaturated compound.

The substituted quinone methide compounds of Formula 1 can be prepared using the following general synthesis scheme.

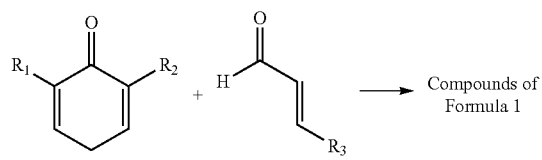

The reaction can take place in the presence of a secondary amine to form a reaction mixture, and water can be removed from the reaction mixture during the reaction. The removal of water drives the reaction toward the products. The reaction mixture can then be contacted with a releasing agent. The definitions of $R_1$, $R_2$, and $R_3$ are defined in connection with Formula 1 above.

The reaction mixture can further comprise a hydrocarbon solvent selected from an aliphatic solvent, an aromatic solvent, and a combination thereof; and water can be removed by azeotropic distillation at a temperature of from 100° C. to 160° C.

The solvent is preferably an aliphatic or aromatic solvent having a boiling point greater than 100° C.

The solvent for the reaction can be n-heptane, ethylbenzene, xylenes, toluene, or a combination thereof.

The secondary amine used in the reaction can be a 5-membered or 6-membered heterocylic compound. Preferably, the secondary amine is morpholine.

The releasing agent can be an acid. Preferably, the acid is p-toluenesulfonic acid, acetic acid, acetic anhydride, or a combination thereof.

The synthesis steps for preparing the compounds of Formula 1 can be carried out in a single reaction vessel.

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, sec-butyl, t-butyl, n-pentyl, i-pentyl, sec-pentyl, t-pentyl, and the like.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl, bicyclo[2.2.2]octanyl and the like. Representative cycloalkyl groups include cyclopropyl, cyclobutyl, cyclopentyl, cyclohexyl, bicyclo[2.2.1]heptanyl, bicyclo[2.2.2]octanyl, and the like.

The terms "aryl" or "ar" as used herein alone or as part of another group (e.g., arylalkyl or alkylaryl) denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(-N($R_A$)($R_B$), wherein $R_A$ and $R_B$ are independently hydrogen, alkyl, or aryl), halo(fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

"Alkylaryl" or "alkaryl" means an aryl group attached to the parent molecule through an alkylene group. The number of carbon atoms in the aryl group and the alkylene group is selected such that there is a total of about 6 to about 18 carbon atoms in the alkaryl group. A preferred alkaryl group is benzyl.

"Vinyl monomer" refers to a monomer comprising at least one carbon-carbon double bond. The monomer can be substituted with various groups, such as acids (e.g., acrylic acid), esters (e.g., acrylate esters), halogen (e.g., vinyl chloride), aryl (e.g., styrene, vinyl toluene, divinylbenzene), cyano (e.g., acrylonitrile), and acetoxy (e.g., vinyl acetate). The monomer can be conjugated (e.g., butadiene, cyclopentadiene, vinyl acetylene, indene, and the like).

A polymerization "inhibitor" refers to a composition of matter that is able to scavenge radicals in a radical polymerization process. Inhibitors can be used to stabilize monomers and prevent their polymerization or quench polymerization when a desired conversion is achieved. They can also be used to regulate or control the kinetics of a polymerization process.

Having described the invention in detail, it will be apparent that modifications and variations are possible without departing from the scope of the invention defined in the appended claims.

EXAMPLES

The foregoing may be better understood by reference to the following examples, which are presented for purposes of illustration and are not intended to limit the scope of the invention.

Example 1: One-Pot Method 2,6-Di-tert-butylphenol (20.192 grams, 96.88 mmoles) and cinnamaldehyde (12.44 mL, 96.88 mmoles) were charged into a 500 mL three-neck round-bottomed flask along with a magnetic follower. The flask was placed on a thermostatted heat block after which the flask was armed with a dropping funnel as well as a Dean-Stark trap and a condenser. A solution of morpholine (8.84 mL, 100 mmoles) in n-heptane (120 mL) was added into the reaction mixture drop wise over 3 hours. To remove water azeotropically, the heating block temperature was set at 145° C. After the addition of the morpholine solution was complete, the reaction was left to progress overnight.

An aliquot of the reaction mixture was analyzed by GC every two hours until there was no further reduction in the peak height of the 2,6-di-tert-butylphenol was observed. The reaction was cooled to room temperature prior to the addition of the releasing agent. Drop wise, acetic acid anhydride was added to the reaction mixture while under vigorous agitation. The reaction mixture was washed with deionized water and the organic layer recovered. Anhydrous magnesium sulfate was used to dry the organic layer. The crude product was recovered after removing the solvent on a rotary evaporator.

A portion of the crude product was dissolved in dichloromethane for the GC analysis of the product. From the test, the product contained unconsumed 2,6-di-tert-butylphenol. An alumina column was used to isolate the quinone methide product by eluting it with n-hexane. Thin-layer chromatography (TLC) was used to analyze the eluted product. The fractions that had a single TLC spot were combined. Once the solvent had been removed, a sample of the product was submitted for GC-MS analysis.

According to GC-MS analysis, the eluted product was pure 2,6-di-tert-butyl-4-(3-phenylallylidene)cyclohexa-2,5-dienone (7-Cinn-QM). Moreover the parent fragment had the molecular weight of 320 g mole$^{-1}$, the expected molecular weight of the 7-Cinn-QM. As the releasing agent, acetic acid anhydride was used in accordance with Nesvadba's method [P. Nesvadba *Synthetic Communication* 30, 2825-2832 (2000)].

Example 2: Two-Pot Method

Into a 500 mL one-neck round-bottomed flask armed with a magnetic follower, 2,6-di-tert-butylphenol (20.602 g: 98.9 mmoles), 20 mL of acetic acid and 50 mL of formic acid were added. The flask was placed in a heating block. After stirring the reaction mixture, cinnamyl alcohol (28.783 g: 98.85 mmoles) was added. The flask was then armed with a water-cooled condenser. The reaction mixture refluxed at 100° C. for 4 hours. Thereafter, the reaction mixture was left to cool down to 25° C. To the flask was added 200 mL of deionized water. The milky solution was then transferred into a separatory funnel. The reaction flask was rinsed with ethyl acetate and the organic washings transferred into the separatory funnel. Additional ethyl acetate was added to the funnel followed by agitation. The aqueous layer was drained off and the organic layer recovered. Anhydrous sodium sulfate was used to dry the ethyl acetate solution. The solvent was removed in vacuo. The resultant crude product containing 4-cinnamyl-2,6-di-tert-butylphenol was a thick oil. No further purification of this product was carried out prior to the oxidation step.

All the crude product (estimated to be 98.85 mmoles) containing 4-cinnamyl-2,6-di-tert-butylphenol was charged into an Erlenmeyer flask followed by tetrahydrofuran (THF). The mixture was stirred using a magnetic stirrer until the crude product was in solution. To the solution was added silver oxide (22.91 grams, 98.85 mmoles). The reaction mixture was stirred at room temperature overnight. Thereafter, the solution was filtered to remove the silver residue. The filtrate was collected and the solvent removed on a rotary evaporator. A minimum amount of acetone was used to dissolve the crude product before the solution was left in a chiller at −10° C. overnight. Light orange crystals were collected and a portion submitted for analysis. According to gas chromatography (GC) analysis of the crystalline product, the purity of the recrystallized product was over 95%. Similarly, the recrystallized product was analyzed by $^1$HMR and $^{13}$CNMR to confirm the structure of the target compound.

Example 3: Screening of Cinnamyl Quinone Methide Compounds

The antipolymerant performance of the isolated cinnamyl quinone methide, 2,6-di-tert-butyl-4-(3-phenylallylidene) cyclohexa-2,5-dienone (7-Cinn-QM), was determined using the static method whereby a 0.31 mM (0.33 mmolal) solution of the retarder was prepared in inhibitor-free styrene. To start with, 4-tert-butylcatechol (TBC) was removed by eluting styrene through alumina. To prepare a 0.31 mM solution of 7-Cinn-QM, 0.0264 g were dissolved in freshly de-inhibited styrene to give a solution of 250 grams. Into twenty-four Ace Glass #15 threaded pressure tubes equipped with PTFE screw caps and fluoroelastomer (FETFE) O-rings, 9 mL of the solution were charged into each tube. To purge as much oxygen out of the solutions as possible, each solution was sparged with nitrogen for 2 minutes. Immediately after sparging each solution, the tube was sealed and the solution kept under a nitrogen gas overhead. In a simulation of the shutdown conditions, the tubes were loaded into a heating block that had been preheated to 120° C. After 30 minutes, and every 15 minutes thereafter, four tubes were retrieved from the block and the polymerization reaction quenched by cooling in an ice bath. The cooled polymer solutions were immediately diluted with toluene.

To measure the amount of polymer formed, methanol was used to precipitate the polymer in accordance with the ASTM D2121 method. The absorbance of the polymer-methanol admixtures were measured at 420 nm. Using a calibration curve, the polymer concentrations in each of the tubes was measured and the four data points for each time were averaged.

Example 4: 7-Phenyl Quinone Methide (7-Ph-QM)

For comparative purpose, 0.0243 g of 7-Ph-QM were dissolved in 350 g of inhibitor-free styrene after which the antipolymerant performance was tested according to the procedure in Example 3.

Similarly, a styrene solution comprising 0.155 mmolal of 7-Ph-QM and 0.155 mmolal of 7-Cinn-QM was used to screen the performance of the combination in accordance with the procedure in Example 3.

Example 5: Untreated Styrene

Immediately after removing TBC from styrene, 9-g aliquots of said styrene were charged into each of the aforementioned pressure tubes. After the dissolved oxygen was purged out of the solutions, polymerization reactions and polymer analysis were conducted in accordance with the procedure in Example 3.

TABLE 1

Treatment of styrene solutions with 0.33 mmolal of antipolymerant for reactions at 122° C. under anaerobic conditions.

| | Polystyrene (%) | | | |
|---|---|---|---|---|
| Time | Untreated | 7-Ph-QM | 7-Cinn-QM | 7-Ph-QM and 7-Cinn-QM |
| 30 | 1.96 | 0.13 | 0.05 | 0.039 |
| 45 | 3.24 | 0.49 | 0.20 | 0.162 |
| 60 | 4.72 | 0.89 | 0.41 | 0.469 |
| 75 | 6.36 | 1.08 | 0.88 | 0.771 |
| 90 | 7.78 | 1.37 | 1.54 | 1.388 |
| 105 | 10.57 | 1.56 | 3.39 | 1.517 |
| 120 | — | 2.4 | 5.13 | 2.42 |
| 135 | — | 3.4 | 7.07 | 3.48 |

When introducing elements of the present invention or the preferred embodiments(s) thereof, the articles "a", "an", "the", and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes can be made in the above compositions and methods without departing from the scope of the invention, it is intended that all matter contained in the above description shall be interpreted as illustrative and not in a limiting sense.

What is claimed is:

1. A method for inhibiting polymerization of a compound comprising an unsaturated carbon-carbon bond, the method comprising contacting said compound with an effective amount of a substituted quinone methide compound of Formula 1:

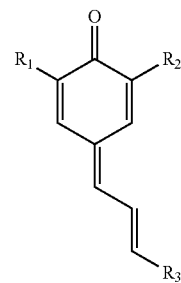

(1)

wherein $R_1$ and $R_2$ are independently hydrogen, $C_4$-$C_{18}$ alkyl, $C_5$-$C_{12}$ cycloalkyl, aryl, $C_7$-$C_{15}$ arylalkyl, or $C_7$-$C_{15}$ alkylaryl; and $R_3$ is hydrogen, $C_1$-$C_{18}$ alkyl, $C_5$-$C_{12}$ cycloalkyl, $C_5$-$C_{12}$ heterocycloalkyl, aryl, $C_7$-$C_{15}$ arylalkyl, or $C_7$-$C_{15}$ alkylaryl; and wherein the substituted quinone methide compound of Formula 1 inhibits polymerization of the compound comprising an unsaturated carbon-carbon bond.

2. The method of claim 1, wherein the aryl group of $R_1$, $R_2$, or $R_3$ is independently -phenylene-$R_4$, where $R_4$ is hydrogen, $C_1$-$C_{18}$ alkyl, $C_5$-$C_{12}$ cycloalkyl, $C_5$-$C_{12}$ heterocycloalkyl, aryl, $C_7$-$C_{15}$ arylalkyl, —COOH and —COOR$_5$, where $R_5$ is $C_1$-$C_{18}$ alkyl, $C_5$-$C_{12}$ cycloalkyl, aryl, $C_7$-$C_{15}$ alkylaryl or $C_7$-$C_{15}$ arylalkyl.

3. The method of claim 1, wherein the aryl group of $R_3$ is -phenylene-$R_4$, where $R_4$ is hydrogen, $C_1$-$C_{18}$ alkyl, $C_5$-$C_{12}$ cycloalkyl, $C_5$-$C_{12}$ heterocycloalkyl, aryl, $C_7$-$C_{15}$ arylalkyl, —COOH and —COOR$_5$, where $R_5$ is $C_1$-$C_{18}$ alkyl, $C_5$-$C_{12}$ cycloalkyl, aryl, $C_7$-$C_{15}$ alkylaryl or $C_7$-$C_{15}$ arylalkyl.

4. The method of claim 1, wherein $R_1$ and $R_2$ are independently $C_4$-$C_{18}$ alkyl, $C_5$-$C_{12}$ cycloalkyl, aryl, or $C_7$-$C_{15}$ arylalkyl.

5. The method of claim 1, wherein $R_1$ and $R_2$ are independently $C_4$-$C_{18}$ alkyl.

6. The method of claim 1, wherein $R_1$ and $R_2$ are independently t-butyl, t-amyl, t-hexyl, t-octyl, and t-decyl.

7. The method of claim 1, wherein $R_1$ and $R_2$ are independently t-butyl, t-amyl, and t-octyl.

8. The method of claim 1, wherein $R_3$ is $C_7$-$C_{15}$ arylalkyl.

9. The method of claim 1, wherein $R_3$ is aryl.

10. The method of claim 9, wherein the aryl group comprises —$C_6H_4$—$R_4$; wherein $R_4$ is hydrogen, $C_1$-$C_3$ alkyl, —COOH and —COOR$_5$, wherein $R_5$ is $C_1$-$C_3$ alkyl, or aryl.

11. The method of claim 1, wherein $R_3$ is phenyl.

12. The method of claim 1, wherein $R_1$ and $R_2$ are independently t-butyl, t-amyl, or t-octyl, and $R_3$ is aryl.

13. The method of claim 1, wherein $R_1$ and $R_2$ are independently t-butyl, t-amyl, or t-octyl, and $R_3$ is phenyl.

14. The method of claim 1, wherein $R_1$ and $R_2$ are t-butyl, and $R_3$ is phenyl.

15. The method of claim 1, further comprising contacting the compound comprising an unsaturated carbon-carbon bond with a phenol, an alkylated phenol, a nitrophenol, a nitrosophenol, a quinone, a hydroquinone, an alkylated hydroquinone, a phenylenediamine, a quinone ether, a quinone methide, a hydroxylamine, a phenothiazine, or a combination thereof in combination with the substituted quinone methide compound of Formula 1.

16. The method of claim 1, wherein the compound comprising an unsaturated carbon-carbon bond is ethylene, propylene, acetylene, styrene, vinyl chloride, vinyl alcohol esters such as vinyl acetate, acrylonitrile, an acrylate ester, a methacrylate ester, acrylic acid, methacrolein, acrolein, butadiene, indene, divinylbenzene, isoprene, acetylene, butylenes, vinyl acetylene, cyclopentadiene, or a combination thereof.

17. The method of claim 16, wherein the compound comprising an unsaturated carbon-carbon bond is ethylene, styrene, an acrylate ester, a methacrylate ester, or a combination thereof.

18. The method of claim 1, wherein the method inhibits polymerization of the hydrocarbon stream in a process of primary fractionation, a process-gas compression, styrene purification, butadiene extraction, transportation, storage, propane dehydrogenation, diesel and petrol fuel stabilization, non-aromatic halogenated vinyl stabilization, olefin metathesis process, hydroxyhydrocarbon purification, or a combination thereof.

19. The method of claim 18, wherein the method inhibits polymerization of the hydrocarbon stream in a process of primary fractionation, styrene purification, butadiene extraction, or a combination thereof.

20. The method of claim 1, wherein the effective amount of the substituted quinone methide compound of Formula 1 is from about 1 ppm to about 10,000 ppm.

* * * * *